United States Patent
Tanikawa et al.

(10) Patent No.: US 6,677,371 B1
(45) Date of Patent: Jan. 13, 2004

(54) 4-OXYBENZOPYRAN DERIVATIVE

(75) Inventors: Keizo Tanikawa, Funabashi (JP); Kazuhiko Ohrai, Funabashi (JP); Kazufumi Yanagihara, Funabashi (JP); Yukihiro Shigeta, Funabashi (JP); Toru Tsukagoshi, Funabashi (JP); Toru Yamashita, Minamisaitama-gun (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 10/069,002

(22) PCT Filed: Oct. 3, 2000

(86) PCT No.: PCT/JP00/06877

§ 371 (c)(1),
(2), (4) Date: Mar. 29, 2002

(87) PCT Pub. No.: WO01/25224

PCT Pub. Date: Apr. 12, 2001

(30) Foreign Application Priority Data

Oct. 5, 1999 (JP) .............................. 11-283861

(51) Int. Cl.$^7$ ..................... A61K 31/35; C07D 311/04
(52) U.S. Cl. ..................... 514/456; 549/399; 549/400; 549/401; 549/403
(58) Field of Search ................. 549/399, 400, 549/401, 403; 514/456

(56) References Cited

U.S. PATENT DOCUMENTS

| | | | | |
|---|---|---|---|---|
| 5,013,853 A | * | 5/1991 | Gericke et al. | 549/401 |
| 5,097,037 A | | 3/1992 | Matsumoto et al. | |
| 5,112,972 A | * | 5/1992 | Gericke et al. | 544/230 |
| 5,387,587 A | * | 2/1995 | Hausler et al. | 514/254 |
| 5,420,314 A | | 5/1995 | Katsuki et al. | |

FOREIGN PATENT DOCUMENTS

| | | |
|---|---|---|
| EP | 0 409 165 A2 | 1/1991 |
| EP | 0 535 377 A2 | 4/1993 |
| GB | 2 204 868 A | 11/1988 |
| JP | 52-91866 | 8/1977 |
| JP | A 56-57785 | 5/1981 |
| JP | A 56-57786 | 5/1981 |
| JP | A 58-67683 | 4/1983 |
| JP | A 58-188880 | 11/1983 |
| JP | A 2-141 | 1/1990 |
| JP | A 3-141286 | 6/1991 |
| JP | A 5-301878 | 11/1993 |
| JP | A 5-507645 | 11/1993 |
| JP | A 7-285983 | 10/1995 |
| JP | A 10-87650 | 4/1998 |
| JP | A 11-209366 | 8/1999 |

OTHER PUBLICATIONS

Evans et al., "Synthesis and Antihypertensive Activity of 6,7–Disubstituted trans–4–Amino–3, 4–dihydro–2, 2–dimethyl–2H–1–benzopyran–3–ols", J.Med.Chem, 27, 1127–1131, 1984.

Ashwood et al., "Synthesis and Antihypertensive Activity of 4–(Cyclic amido)–2H–1–benzopyrans", J.Med.Chem, 29, 2194–2201, 1986.

North et al., "Synthesis of 6–Cyano–2, 2–dimethyl–2H–1 benzopyran and Other Substituted 2, 2–Dimethyl–2H–1 benzopyrans", J.Org.Chem, 60, 3397–3400, 1995.

Chemical Abstracts, vol. 126, No. 17, 1997, Sun, Hong Bin, "Facile Synthesis", p. 566.

Hong Bin Sun et al., "Facile Synthesis of trans–3,4–Diol Derivatives of Substituted Chromans via Catalytic Epoxidation", Chinese Chemical Letters, vol. 8, No. 1, pp. 1–4, 1997.

\* cited by examiner

*Primary Examiner*—Alan L. Rotman
*Assistant Examiner*—Raymond Covington
(74) *Attorney, Agent, or Firm*—Oliff & Berridge, PLC

(57) ABSTRACT

This invention relates to a 4-oxybenzopyran derivative of formula (I) wherein, $R^1$ and $R^2$ represent each independently a hydrogen atom, a $C_{1-6}$ alkyl group or a phenyl group; $R^3$ represents a hydroxyl group or $C_{1-6}$ alkylcarbonyloxy group; $R^4$ represents a hydrogen atom, a $C_{3-6}$ cycloalkyl group, a $C_{1-6}$ alkyl group, a $C_{1-6}$ alkylcarbonyl group, a $C_{1-6}$ alkylaminocarbonyl group, a di-$C_{1-6}$ alkylaminocarbonyl group, an aryl group or a heteroaryl group; $R^5$ represents a hydrogen atom or a $C_{1-6}$ alkyl group; X is absent or represents C=O or $SO_2$; $R^6$ represents a hydrogen atom, a $C_{1-6}$ alkyl group or a $C_{3-6}$ cycloalkyl group; $R^7$ represents a hydrogen atom, a halogen atom, a nitro group or a cyano group; or a pharmaceutically acceptable salt thereof. And this invention also relates to a drug for treating arrhytmia having the prolongation effect on the functional refractory period comprising said compound or a pharmaceutically acceptable salt thereof as an active ingredient.

(I)

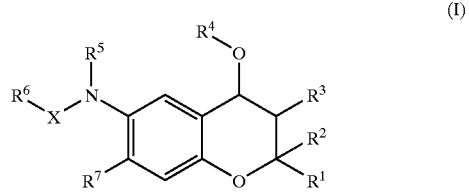

6 Claims, No Drawings

4-OXYBENZOPYRAN DERIVATIVE

TECHNICAL FIELD

The present invention relates to 4-oxybenzopyran derivatives having a prolongation effect on the functional refractory period, which are used for treatments of arrhythmia in mammal including human beings.

BACKGROUND ART

As benzopyran derivatives, there have been known 4-acylaminobenzopyran derivatives exemplified by Cromakalim (Japanese Patent Application Laid-Open No. Sho 58-67683). These 4-acylaminobenzopyran derivatives exemplified by Cromakalim are known to open an ATP sensitive K$^+$ channel and to be effective for the treatment of hypertension or asthma, but there has not been any mention as to the treatment for arrhythmia based on the prolongation effect on the functional refractory period.

Now, conventional antiarrhythmic agents having the prolongation effect on the functional refractory period as a main function (such as Class I drugs of antiarrhythmic agent classification according to Vaughan Williams, or d-sotalol belonging to Class III) have highly dangerous arrhythmic inducing actions that can result in sudden death such as torsades de pointes based on extension of ventricular muscle action potential relating to the prolongation effect on the functional refractory period, which become the therapeutic problems. Thus, agents having less side effects are desired.

The inventors of the present invention have made an intensive study of compounds having the prolongation effect on the functional refractory period more selective for atrium muscle than for ventricular muscle, and found that the compound of the general formula (I) has a prolongation effect on the functional refractory period selective for atrium muscle without any influence on the refractory period of ventricular muscle and action potential parameters.

DISCLOSURE OF INVENTION

The inventors of the present invention have studied eagerly 4-oxybenzopyran derivatives, and found that the compound of the formula (I) has the strong prolongation effect on the functional refractory period, and it is useful as an antiarrhythmic agent. The present invention has been made based on this finding.

The present invention relates to a 4-oxybenzopyran derivative of the formula (I)

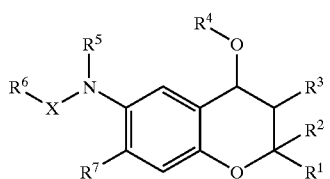

(I)

wherein, $R^1$ and $R^2$ represent each independently a hydrogen atom; a $C_{1-6}$ alkyl group in which said alkyl group may be optionally substituted with a halogen atom, a $C_{1-6}$ alkoxy group or a hydroxyl group; or a phenyl group in which said phenyl group may be optionally substituted with a halogen atom, a hydroxyl group, a nitro group, a cyano group, a $C_{1-6}$ alkyl group or a $C_{1-6}$ alkoxy group;

$R^3$ represents a hydroxyl group or a $C_{1-6}$ alkylcarbonyloxy group;

$R^4$ represents a hydrogen atom, a $C_{3-6}$ cycloalkyl group, a $C_{1-6}$ alkyl group, a $C_{1-6}$ alkylcarbonyl group, a $C_{1-6}$ alkylaminocarbonyl group or a di-$C_{1-6}$ alkylaminocarbonyl group in which said $C_{1-6}$ alkyl group, said $C_{1-6}$ alkylcarbonyl group, said $C_{1-6}$ alkylaminocarbonyl group and said di-$C_{1-6}$ alkylaminocarbonyl group may be each optionally substituted with a halogen atom, a $C_{1-6}$ alkoxy group, a $C_{1-6}$ alkoxy group substituted by a halogen atom; a carboxyl group, a $C_{1-6}$ alkoxycarbonyl group, a hydroxyl group, an aryl group or a heteroaryl group; in which said aryl group and said heteroaryl group may be optionally substituted with $(R^8)_m$, in which $R^8$ represents a halogen atom, a hydroxyl group, a $C_{1-6}$ alkyl group, a $C_{1-6}$ alkyl group substituted by a halogen atom or a $C_{1-6}$ alkoxy group; a $C_{1-6}$ alkoxy group, a $C_{1-6}$ alkoxy group substituted by a halogen atom; or $R^8$ represents a nitro group, a cyano group, a formyl group, a formamide group, an amino group, a $C_{1-6}$ alkylamino group, a di-$C_{1-6}$ alkylamino group, a $C_{1-6}$ alkylcarbonylamino group, a $C_{1-6}$ alkylsulfonylamino group, an aminocarbonyl group, a $C_{1-6}$ alkylaminocarbonyl group, a di-$C_{1-6}$ alkylaminocarbonyl group, a $C_{1-6}$ alkylcarbonyl group, a $C_{1-6}$ alkoxycarbonyl group, an aminosulfonyl group, a $C_{1-6}$ alkylsulfonyl group, a carboxyl group or an arylcarbonyl group, m represents an integer of 1–3 and each $R^8$ may same or different if m represents 2 or 3; or $R^4$ represents an aryl group or a heteroaryl group in which said aryl group and said heteroaryl group may be optionally substituted with $(R^9)_n$ in which $R^9$ has the same meaning as $R^8$, n represents an integer of 1–3, and each $R^9$ may be same or different if n represents 2 or 3;

$R^5$ represents a hydrogen atom or a $C_{1-6}$ alkyl group;

X is absent or represents C=O or $SO_2$;

$R^6$ represents a hydrogen atom, a $C_{1-6}$ alkyl group in which said alkyl group may be optionally substituted with a halogen atom, a hydroxyl group or a $C_{1-6}$ alkoxy group; or a $C_{3-6}$ cycloalkyl group;

$R^7$ represents a hydrogen atom, a halogen atom, a nitro group or a cyano group;

or a pharmaceutically acceptable salt thereof.

The compound according to the present invention has the strong prolongation effect on the functional refractory period and it can be used as a drug for treating arrhythmia.

Respective substituents for the compound (I) according to the present invention are illustrated specifically as follows.

Herein, "n" means normal, "i" means iso, "s" means secondary, "t" means tertiary, "c" means cyclo, "o" means ortho, "m" means meta, and "p" means para.

As $C_{1-6}$ alkyl groups, there may be mentioned methyl, ethyl, n-propyl, i-propyl, n-butyl, i-butyl, s-butyl, t-butyl, 1-pentyl, 2-pentyl, 3-pentyl, i-pentyl, neopentyl, 2,2-dimethylpropyl, 1-hexyl, 2-hexyl, 3-hexyl, 1-methyl-n-pentyl, 1,1,2-trimethyl-n-propyl, 1,2,2-trimethyl-n-propyl, 3,3-dimethyl-n-butyl, trifluoromethyl, trifluoroethyl, pentafluoroethyl, cyanomethyl and hydroxymethyl, etc.

Preferably, there may be mentioned methyl, ethyl, n-propyl, i-propyl and n-butyl.

As halogen atoms, there may be mentioned a fluorine atom, a chlorine atom, a bromine atom and an iodine atom. Preferably, there may be mentioned a fluorine atom, a chlorine atom and a bromine atom.

As $C_{1-6}$ alkoxy groups, there may be mentioned methoxy, trifluoromethoxy, ethoxy, n-propoxy, i-propoxy, n-butoxy, i-butoxy, s-butoxy, t-butoxy, 1-pentyloxy, 2-pentyloxy, 3-pentyloxy, i-pentyloxy, neopentyloxy, 2,2-dimethylpropoxy, 1-hexyloxy, 2-hexyloxy, 3-hexyloxy, 1-methyl-n-pentyloxy, 1,1,2-trimethyl-n-propoxy, 1,2,2-trimethyl-n-propoxy and 3,3-dimethyl-n-butoxy, etc.

Preferably, there may be mentioned methoxy, ethoxy, n-propoxy and i-propoxy.

As $C_{1-6}$ alkylcarbonyloxy groups, there may be mentioned methylcarbonyloxy, ethylcarbonyloxy, n-propylcarbonyloxy, i-propylcarbonyloxy, n-butylcarbonyloxy, i-butylcarbonyloxy, s-butylcarbonyloxy, t-butylcarbonyloxy, 1-pentylcarbonyloxy, 2-pentylcarbonyloxy, 3-pentylcarbonyloxy, i-pentylcarbonyloxy, neopentylcarbonyloxy, t-pentylcarbonyloxy, 1-hexylcarbonyloxy, 2-hexylcarbonyloxy, 3-hexylcarbonyloxy, 1-methyl-n-pentylcarbonyloxy, 1,1,2-trimethyl-n-propylcarbonyloxy, 1,2,2-trimethyl-n-propylcarbonyloxy and 3,3-dimethyl-n-butylcarbonyloxy, etc.

Preferably, there may be mentioned methylcarbonyloxy, ethylcarbonyloxy, n-propylcarbonyloxy, i-propylcarbonyloxy, n-butylcarbonyloxy and t-butylcarbonyloxy.

As $C_{3-6}$ cycloalkyl groups, there may be mentioned cyclopropyl, cyclobutyl, cyclopentyl, cyclohexyl, cycloheptyl and cyclooctyl, etc.

Preferably, there may be mentioned cyclopropyl, cyclobutyl and cyclohexyl.

As $C_{1-6}$ alkylcarbonyl groups, there may be mentioned methylcarbonyl, ethylcarbonyl, n-propylcarbonyl, i-propylcarbonyl, n-butylcarbonyl, i-butylcarbonyl, s-butylcarbonyl, t-butylcarbonyl, 1-pentylcarbonyl, 2-pentylcarbonyl, 3-pentylcarbonyl, i-pentylcarbonyl, neopentylcarbonyl, t-pentylcarbonyl, 1-hexylcarbonyl, 2-hexylcarbonyl and 3-hexylcarbonyl.

Preferably, there may be mentioned methylcarbonyl, ethylcarbonyl, n-propylcarbonyl, i-propylcarbonyl and n-butylcarbonyl.

As $C_{1-6}$ alkylaminocarbonyl groups, there may be mentioned methylaminocarbonyl, ethylaminocarbonyl, n-propylaminocarbonyl, i-propylaminocarbonyl, n-butylaminocarbonyl, i-butylaminocarbonyl, s-butylaminocarbonyl, t-butylaminocarbonyl, 1-pentylaminocarbonyl, 2-pentylaminocarbonyl, 3-pentylaminocarbonyl, i-pentylaminocarbonyl, neopentylaminocarbonyl, t-pentylaminocarbonyl, 1-hexylaminocarbonyl, 2-hexylaminocarbonyl and 3-hexylaminocarbonyl, etc.

Preferably, there may be mentioned methylaminocarbonyl, ethylaminocarbonyl, n-propylaminocarbonyl, i-propylaminocarbonyl and n-butylaminocarbonyl.

As di-$C_{1-6}$ alkylaminocarbonyl groups, there may be mentioned dimethylaminocarbonyl, diethylaminocarbonyl, di-n-propylaminocarbonyl, di-i-propylaminocarbonyl, di-c-propylaminocarbonyl, di-n-butylaminocarbonyl, di-i-butylaminocarbonyl, di-s-butylaminocarbonyl, di-t-butylaminocarbonyl, di-c-butylaminocarbonyl, di-1-pentylaminocarbonyl, di-2-pentylaminocarbonyl, di-3-pentylaminocarbonyl, di-i-pentylaminocarbonyl, di-neopentylaminocarbonyl, di-t-pentylaminocarbonyl, di-c-pentylaminocarbonyl, di-1-hexylaminocarbonyl, di-2-hexylaminocarbonyl and di-3-hexylaminocarbonyl, etc.

Preferably, there may be mentioned dimethylaminocarbonyl, diethylaminocarbonyl, di-n-propylaminocarbonyl, di-i-propylaminocarbonyl, di-c-propylaminocarbonyl and di-n-butylaminocarbonyl.

As $C_{1-6}$ alkoxycarbonyl groups, there may be mentioned methoxycarbonyl, ethoxycarbonyl, n-propoxycarbonyl, i-propoxycarbonyl, n-butoxycarbonyl, i-butoxycarbonyl, s-butoxycarbonyl, t-butoxycarbonyl, 1-pentyloxycarbonyl, 2-pentyloxycarbonyl, 3-pentyloxycarbonyl, i-pentyloxycarbonyl, neopentyloxycarbonyl, t-pentyloxycarbonyl, 1-hexyloxycarbonyl, 2-hexyloxycarbonyl and 3-hexyloxycarbonyl, etc.

Preferably, there may be mentioned methoxycarbonyl, ethoxycarbonyl, n-propoxycarbonyl, i-propoxycarbonyl, n-butoxycarbonyl, i-butoxycarbonyl, s-butoxycarbonyl and t-butoxycarbonyl.

As aryl groups, there may be mentioned phenyl, biphenyl, naphthyl, anthryl and phenanthryl etc.

Preferably, there may be mentioned phenyl, biphenyl and naphthyl.

As heteroaryl groups, there may be mentioned 2-thienyl, 3-thienyl, 2-furyl, 3-furyl, 2-pyranyl, 3-pyranyl, 4-pyranyl, 2-benzofuranyl, 3-benzofuranyl, 4-benzofuranyl, 5-benzofuranyl, 6-benzofuranyl, 7-benzofuranyl, 1-isobenzofuranyl, 4-isobenzofuranyl, 5-isobenzofuranyl, 2-benzothienyl, 3-benzothienyl, 4-benzothienyl, 5-benzothienyl, 6-benzothienyl, 7-benzothienyl, 1-isobenzothienyl, 4-isobenzothienyl, 5-isobenzothienyl, 2-chromenyl, 3-chromenyl, 4-chromenyl, 5-chromenyl, 6-chromenyl, 7-chromenyl, 8-chromenyl, 1-pyrrolyl, 2-pyrrolyl, 3-pyrrolyl, 1-imidazolyl, 2-imidazolyl, 4-imidazolyl, 1-pyrazolyl, 3-pyrazolyl, 4-pyrazolyl, 2-thiazolyl, 4-thiazolyl, 5-thiazolyl, 3-isothiazolyl, 4-isothiazolyl, 5-isothiazolyl, 2-oxazolyl, 4-oxazolyl, 5-oxazolyl, 3-isoxazolyl, 4-isoxazolyl, 5-isoxazolyl, 2-pyridyl, 3-pyridyl, 4-pyridyl, 2-pyrazinyl, 2-pyrimidinyl, 4-pyrimidinyl, 5-pyrimidinyl, 3-pyridazinyl, 4-pyridazinyl, 1-indolizinyl, 2-indolizinyl, 3-indolizinyl, 5-indolizinyl, 6-indolizinyl, 7-indolizinyl, 8-indolizinyl, 1-isoindolyl, 4-isoindolyl, 5-isoindolyl, 1-indolyl, 2-indolyl, 3-indolyl, 4-indolyl, 5-indolyl, 6-indolyl, 7-indolyl, 1-indazolyl, 2-indazolyl, 3-indazolyl, 4-indazolyl, 5-indazolyl, 6-indazolyl, 7-indazolyl, 1-purinyl, 2-purinyl, 3-purinyl, 6-purinyl, 7-purinyl, 8-purinyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 1-phthalazinyl, 5-phthalazinyl, 6-phthalazinyl, 2-naphthyridinyl, 3-naphthyridinyl, 4-naphthyridinyl, 2-quinoxalinyl, 5-quinoxalinyl, 6-quinoxalinyl, 2-quinazolinyl, 4-quinazolinyl, 5-quinazolinyl, 6-quinazolinyl, 7-quinazolinyl, 8-quinazolinyl, 3-cinnolinyl, 4-cinnolinyl, 5-cinnolinyl, 6-cinnolinyl, 7-cinnolinyl, 8-cinnolinyl, 2-pteridinyl, 4-pteridinyl, 6-pteridinyl, 7-pteridinyl and 3-furazanyl, etc.

Preferably, there may be mentioned 2-pyridyl, 3-pyridyl and 4-pyridyl, etc.

As $C_{1-6}$ alkylamino groups, there may be mentioned methylamino, ethylamino, n-propylamino, i-propylamino, c-propylamino, n-butylamino, i-butylamino, s-butylamino, t-butylamino, c-butylamino, 1-pentylamino, 2-pentylamino, 3-pentylamino, i-pentylamino, neopentylamino, t-pentylamino, c-pentylamino, 1-hexylamino, 2-hexylamino, 3-hexylamino, c-hexylamino, 1-methyl-n-pentylamino, 1,1,2-trimethyl-n-propylamino, 1,2,2-trimethyl-n-propylamino and 3,3-dimethyl-n-butylamino, etc.

Preferably, there may be mentioned methylamino, ethylamino, n-propylamino, i-propylamino and n-butylamino.

As di-$C_{1-6}$ alkylamino groups, there may be mentioned dimethylamino, diethylamino, di-n-propylamino, di-i-propylamino, di-c-propylamino, di-n-butylamino, di-i-butylamino, di-s-butylamino, di-t-butylamino, di-c-butylamino, di-1-pentylamino, di-2-pentylamino, di-3- pentylamino, di-i-pentylamino, di-neopentylamino, di-t-pentylamino, di-c-pentylamino, di-1-hexylamino, di-2-hexylamino, di-3-hexylamino, di-c-hexylamino, di-(1-methyl-n-pentyl)amino, di-(1,1,2-trimethyl-n-propyl)amino, di-(1,2,2-trimethyl-n-propyl)amino, di-(3,3-dimethyl-n-butyl)amino, methyl(ethyl)amino, methyl(n-propyl)amino, methyl(i-propyl)amino, methyl(c-propyl)amino, methyl(n-butyl)amino, methyl(i-butyl)amino, methyl(s-butyl)amino, methyl(t-butyl)amino, methyl(c-butyl)amino, ethyl(n-propyl)amino, ethyl(i-propyl)amino, ethyl(c-propyl)amino, ethyl(n-butyl)amino, ethyl(i-butyl)amino, ethyl(s-butyl)amino, ethyl(t-butyl)amino, ethyl(c-butyl)amino, n-propyl(i-propyl)amino, n-propyl(c-propyl)amino, n-propyl(n-butyl)amino, n-propyl(i-butyl)amino, n-propyl(s-butyl)amino, n-propyl(t-butyl)amino, n-propyl(c-butyl)amino, i-propyl(c-propyl)amino, i-propyl(n-butyl)amino, i-propyl(i-butyl)amino, i-propyl(s-butyl)amino, i-propyl(t-butyl)amino, i-propyl(c-butyl)amino, c-propyl(n-butyl)amino, c-propyl(i-butyl)amino, c-propyl(s-butyl)amino, c-propyl(t-butyl)amino, c-propyl(c-butyl)amino, n-butyl(i-butyl)amino, n-butyl(s-butyl)amino, n-butyl(t-butyl)amino, n-butyl(c-butyl)amino, i-butyl (s-butyl)amino, i-butyl(t-butyl)amino, i-butyl(c-butyl)amino, s-butyl(t-butyl)amino, s-butyl(c-butyl)amino and t-butyl(c-butyl) amino, etc.

Preferably, there may be mentioned dimethylamino, diethylamino, di-n-propylamino, di-i-propylamino and di-n-butylamino.

As $C_{1-6}$ alkylcarbonylamino groups, there may be mentioned methylcarbonylamino, ethylcarbonylamino, n-propylcarbonylamino, i-propylcarbonylamino, n-butylcarbonylamino, i-butylcarbonylamino, s-butylcarbonylamino, t-butylcarbonylamino, 1-pentylcarbonylamino, 2-pentylcarbonylamino, 3-pentylcarbonylamino, i-pentylcarbonylamino, neopentylcarbonylamino, t-pentylcarbonylamino, 1-hexylcarbonylamino, 2-hexylcarbonylamino and 3-hexylcarbonylamino, etc.

Preferably, there may be mentioned methylcarbonylamino, ethylcarbonylamino, n-propylcarbonylamino, i-propylcarbonylamino and n-butylcarbonylamino.

As $C_{1-6}$ alkylsulfonylamino groups, there may be mentioned methylsulfonylamino, ethylsulfonylamino, n-propylsulfonylamino, i-propylsulfonylamino, n-butylsulfonylamino, i-butylsulfonylamino, s-butylsulfonylamino, t-butylsulfonylamino, 1-pentylsulfonylamino, 2-pentylsulfonylamino, 3-pentylsulfonylamino, i-pentylsulfonylamino, neopentylsulfonylamino, t-pentylsulfonylamino, 1-hexylsulfonylamino, 2-hexylsulfonylamino and 3-hexylsulfonylamino, etc.

Preferably, there may be mentioned methylsulfonylamino, ethylsulfonylamino, n-propylsulfonylamino, i-propylsulfonylamino and n-butylsulfonylamino.

As $C_{1-6}$ alkylsulfonyl groups, there may be mentioned methanesulfonyl and ethanesulfonyl.

As arylcarbonyl groups, there may be mentioned benzoyl, p-methylbenzoyl, p-t-butylbenzoyl, p-methoxybenzoyl, p-chlorobenzoyl, p-nitrobenzoyl and p-cyanobenzoyl.

Preferably, there may be mentioned benzoyl, p-nitrobenzoyl and p-cyanobenzoyl.

As preferable compounds used in the present invention, the following compounds may be mentioned.

(1) A 4-oxybenzopyran derivative or pharmaceutically acceptable salt thereof according to formula(I), wherein $R^1$ and $R^2$ represent both methyl groups and $R^3$ represents a hydroxyl group.

(2) A 4-oxybenzopyran derivative or pharmaceutically acceptable salt thereof according to the aforementioned (1), wherein X represents C=O and $R^5$ represents a hydrogen atom.

(3) A 4-oxybenzopyran derivative or pharmaceutically acceptable salt thereof according to the aforementioned (2), wherein $R^4$ represents an alkyl group and $R^7$ represents a nitro group.

Specific examples of the compounds that can be used in the present invention are shown as follows, but the present invention is not limited thereto. Herein, "Me" means a methyl group, "Et" means an ethyl group, "Pr" means a propyl group, "Bu" means a butyl group, "Pen" means a pentyl group, "Hex" means a hexyl group, "Ph" means a phenyl group, "Ac" means an acetyl group ($COCH_3$), and "—" means a bond, respectively.

TABLE 1

| $R^1$ | $R^2$ | $R^3$ | $R^4$ | $R^5$ | $R_7$ |
|---|---|---|---|---|---|
| H | H | OH | i-Pr | H | H |
| Me | Me | OH | c-Pr | H | H |
| Me | Me | OH | c-Hex | H | H |
| Me | Me | OH | Me | H | H |
| Me | Me | OH | Et | H | H |
| Me | Me | OH | n-Pr | H | H |
| Me | Me | OH | i-Pr | H | H |
| Me | Me | OH | n-Bu | H | H |
| Me | Me | OH | n-Pen | H | $NO_2$ |
| Me | Me | OH | n-Hex | H | $NO_2$ |
| Me | Me | OH | COMe | H | $NO_2$ |
| Me | Me | OH | CONHMe | H | $NO_2$ |
| Me | Me | OH | $CONMe_2$ | H | $NO_2$ |
| Me | Me | OCOMe | $CF_3$ | H | $NO_2$ |
| Me | Me | OCOEt | $CH_2Ph$ | H | $NO_2$ |
| Me | Me | OH | $CH_2CH_2Ph$ | H | $NO_2$ |
| Me | Me | OH | $CH_2CH_2Ph$ | Et | $NO_2$ |
| Me | Me | OH | $CH_2CH_2Ph$ | n-Pr | $NO_2$ |
| Ph | Ph | OH | $CH_2CH_2Ph$ | i-Pr | $NO_2$ |
| Et | Et | OH | $CH_2CH_2Ph$ | n-Bu | $NO_2$ |
| Me | Me | OH | $CH_2CH_2Ph$ | H | H |
| i-Pr | i-Pr | OH | $CH_2CH_2Ph$ | t-Bu | $NO_2$ |
| n-Bu | n-Bu | OH | $CH_2CH_2Ph$ | n-Pen | $NO_2$ |
| i-Bu | i-Bu | OH | $CH_2CH_2Ph$ | n-Hex | $NO_2$ |
| t-Bu | t-Bu | OH | $CH_2CH_2Ph$ | Me | $NO_2$ |
| n-Pen | n-Pen | OH | $CH_2CH_2Ph$ | H | Cl |
| n-Hex | n-Hex | OH | $CH_2CH_2Ph$ | H | F |
| $CF_3$ | $CF_3$ | OH | $CH_2CH_2Ph$ | H | Br |
| $CH_2OCH_3$ | $CH_2OCH_3$ | OH | $CH_2CH_2Ph$ | H | CN |

TABLE 2

Structure: chroman with F₃C-C(=O)-N(R⁵)- at 6-position, R⁷ at 7-position, R⁴O at 4-position, R³ at 3-position, R² and R¹ at 2-position.

| R¹ | R² | R³ | R⁴ | R⁵ | R⁷ |
|---|---|---|---|---|---|
| H | H | OH | i-Pr | H | H |
| Me | Me | OH | c-Pr | H | H |
| Me | Me | OH | c-Hex | H | H |
| Me | Me | OH | Me | H | H |
| Me | Me | OH | Et | H | H |
| Me | Me | OH | n-Pr | H | H |
| Me | Me | OH | i-Pr | H | H |
| Me | Me | OH | n-Bu | H | H |
| Me | Me | OH | n-Pen | H | NO₂ |
| Me | Me | OH | n-Hex | H | NO₂ |
| Me | Me | OH | COMe | H | NO₂ |
| Me | Me | OH | CONHMe | H | NO₂ |
| Me | Me | OH | CONMe₂ | H | NO₂ |
| Me | Me | OCOMe | CF₃ | H | NO₂ |
| Me | Me | OCOEt | CH₂Ph | H | NO₂ |
| Me | Me | OH | CH₂CH₂Ph | H | H |
| Me | Me | OH | CH₂CH₂Ph | Et | NO₂ |
| Me | Me | OH | CH₂CH₂Ph | n-Pr | NO₂ |
| Ph | Ph | OH | CH₂CH₂Ph | i-Pr | NO₂ |
| Et | Et | OH | CH₂CH₂Ph | n-Bu | NO₂ |
| Me | Me | OH | CH₂CH₂Ph | H | H |
| i-Pr | i-Pr | OH | CH₂CH₂Ph | t-Bu | NO₂ |
| n-Bu | n-Bu | OH | CH₂CH₂Ph | n-Pen | NO₂ |
| i-Bu | i-Bu | OH | CH₂CH₂Ph | n-Hex | NO₂ |
| t-Bu | t-Bu | OH | CH₂CH₂Ph | Me | NO₂ |
| n-Pen | n-Pen | OH | CH₂CH₂Ph | H | Cl |
| n-Hex | n-Hex | OH | CH₂CH₂Ph | H | F |
| CF₃ | CF₃ | OH | CH₂CH₂Ph | H | Br |
| CH₂OCH₃ | CH₂OCH₃ | OH | CH₂CH₂Ph | H | CN |

TABLE 3

Structure: chroman with Me-SO₂-N(R⁵)- at 6-position, R⁷ at 7-position, R⁴O at 4-position, R³ at 3-position, R² and R¹ at 2-position.

| R¹ | R² | R³ | R⁴ | R⁵ | R⁷ |
|---|---|---|---|---|---|
| H | H | OH | i-Pr | H | H |
| Me | Me | OH | c-Pr | H | H |
| Me | Me | OH | c-Hex | H | H |
| Me | Me | OH | Me | H | H |
| Me | Me | OH | Et | H | H |
| Me | Me | OH | n-Pr | H | H |
| Me | Me | OH | i-Pr | H | H |
| Me | Me | OH | n-Bu | H | H |
| Me | Me | OH | n-Pen | H | NO₂ |
| Me | Me | OH | n-Hex | H | NO₂ |
| Me | Me | OH | COMe | H | NO₂ |
| Me | Me | OH | CONHMe | H | NO₂ |
| Me | Me | OH | CONMe₂ | H | NO₂ |
| Me | Me | OCOMe | CF₃ | H | NO₂ |
| Me | Me | OCOEt | CH₂Ph | H | NO₂ |
| Me | Me | OH | CH₂CH₂Ph | Me | NO₂ |
| Me | Me | OH | CH₂CH₂Ph | Et | NO₂ |
| Me | Me | OH | CH₂CH₂Ph | n-Pr | NO₂ |
| Ph | Ph | OH | CH₂CH₂Ph | i-Pr | NO₂ |
| Et | Et | OH | CH₂CH₂Ph | n-Bu | NO₂ |
| n-Pr | n-Pr | OH | CH₂CH₂Ph | i-Bu | NO₂ |
| i-Pr | i-Pr | OH | CH₂CH₂Ph | t-Bu | NO₂ |
| n-Bu | n-Bu | OH | CH₂CH₂Ph | n-Pen | NO₂ |
| i-Bu | i-Bu | OH | CH₂CH₂Ph | n-Hex | NO₂ |
| t-Bu | t-Bu | OH | CH₂CH₂Ph | Me | NO₂ |
| n-Pen | n-Pen | OH | CH₂CH₂Ph | H | Cl |
| n-Hex | n-Hex | OH | CH₂CH₂Ph | H | F |
| CF₃ | CF₃ | OH | CH₂CH₂Ph | H | Br |
| CH₂OCH₃ | CH₂OCH₃ | OH | CH₂CH₂Ph | H | CN |

TABLE 4

Structure: chroman with Et-N(R⁵)- at 6-position, R⁷ at 7-position, R⁴O at 4-position, R³ at 3-position, R² and R¹ at 2-position.

| R¹ | R² | R³ | R⁴ | R⁵ | R⁷ |
|---|---|---|---|---|---|
| H | H | OH | i-Pr | H | H |
| Me | Me | OH | c-Pr | H | H |
| Me | Me | OH | c-Hex | H | H |
| Me | Me | OH | Me | H | H |
| Me | Me | OH | Et | H | H |
| Me | Me | OH | n-Pr | H | H |
| Me | Me | OH | i-Pr | H | H |
| Me | Me | OH | n-Bu | H | H |
| Me | Me | OH | n-Pen | H | NO₂ |
| Me | Me | OH | n-Hex | H | NO₂ |
| Me | Me | OH | COMe | H | NO₂ |
| Me | Me | OH | CONHMe | H | NO₂ |
| Me | Me | OH | CONMe₂ | H | NO₂ |
| Me | Me | OCOMe | CF₃ | H | NO₂ |
| Me | Me | OCOEt | CH₂Ph | H | NO₂ |
| Me | Me | OH | CH₂CH₂Ph | Me | NO₂ |
| Me | Me | OH | CH₂CH₂Ph | Et | NO₂ |
| Me | Me | OH | CH₂CH₂Ph | n-Pr | NO₂ |
| Ph | Ph | OH | CH₂CH₂Ph | i-Pr | NO₂ |
| Et | Et | OH | CH₂CH₂Ph | n-Bu | NO₂ |
| n-Pr | n-Pr | OH | CH₂CH₂Ph | i-Bu | NO₂ |
| i-Pr | i-Pr | OH | CH₂CH₂Ph | t-Bu | NO₂ |
| n-Bu | n-Bu | OH | CH₂CH₂Ph | n-Pen | NO₂ |
| i-Bu | i-Bu | OH | CH₂CH₂Ph | n-Hex | NO₂ |
| t-Bu | t-Bu | OH | CH₂CH₂Ph | Me | NO₂ |
| n-Pen | n-Pen | OH | CH₂CH₂Ph | H | Cl |
| n-Hex | n-Hex | OH | CH₂CH₂Ph | H | F |
| CF₃ | CF₃ | OH | CH₂CH₂Ph | H | Br |
| CH₂OCH₃ | CH₂OCH₃ | OH | CH₂CH₂Ph | H | CN |

TABLE 5

| $R^1$ | $R^2$ | $R^3$ | $R^4$ | $R^5$ | $R^7$ |
|---|---|---|---|---|---|
| H | H | OH | i-Pr | H | H |
| Me | Me | OH | c-Pr | H | H |
| Me | Me | OH | c-Hex | H | H |
| Me | Me | OH | Me | H | H |
| Me | Me | OH | Et | H | H |
| Me | Me | OH | n-Pr | H | H |
| Me | Me | OH | i-Pr | H | H |
| Me | Me | OH | n-Bu | H | H |
| Me | Me | OH | n-Pen | H | $NO_2$ |
| Me | Me | OH | n-Hex | H | $NO_2$ |
| Me | Me | OH | COMe | H | $NO_2$ |
| Me | Me | OH | CONHMe | H | $NO_2$ |
| Me | Me | OH | $CONMe_2$ | H | $NO_2$ |
| Me | Me | OCOMe | $CF_3$ | H | $NO_2$ |
| Me | Me | OCOEt | $CH_2Ph$ | H | $NO_2$ |
| Me | Me | OH | $CH_2CH_2Ph$ | H | $NO_2$ |
| Me | Me | OH | $CH_2CH_2Ph$ | Et | $NO_2$ |
| Me | Me | OH | $CH_2CH_2Ph$ | n-Pr | $NO_2$ |
| Ph | Ph | OH | $CH_2CH_2Ph$ | i-Pr | $NO_2$ |
| Et | Et | OH | $CH_2CH_2Ph$ | n-Bu | $NO_2$ |
| Me | Me | OH | $CH_2CH_2Ph$ | H | H |
| i-Pr | i-Pr | OH | $CH_2CH_2Ph$ | t-Bu | $NO_2$ |
| n-Bu | n-Bu | OH | $CH_2CH_2Ph$ | n-Pen | $NO_2$ |
| i-Bu | i-Bu | OH | $CH_2CH_2Ph$ | n-Hex | $NO_2$ |
| t-Bu | t-Bu | OH | $CH_2CH_2Ph$ | Me | $NO_2$ |
| n-Pen | n-Pen | OH | $CH_2CH_2Ph$ | H | Cl |
| n-Hex | n-Hex | OH | $CH_2CH_2Ph$ | H | F |
| $CF_3$ | $CF_3$ | OH | $CH_2CH_2Ph$ | H | Br |
| $CH_2OCH_3$ | $CH_2OCH_3$ | OH | $CH_2CH_2Ph$ | H | CN |

TABLE 6

| $R^6$ | $R^7$ | $R^8$ | n |
|---|---|---|---|
| H | H | p-MeO | 0 |
| H | H | p-MeO | 1 |
| H | H | p-MeO | 2 |
| Me | H | p-MeO | 3 |
| Me | H | p-MeO | 4 |
| Me | H | m-MeO | 0 |
| Me | H | o-MeO | 1 |
| $CF_3$ | H | p-Me | 2 |
| t-Bu | $NO_2$ | p-Et | 3 |
| t-Bu | $NO_2$ | m-Et | 4 |
| t-Bu | $NO_2$ | o-Et | 2 |
| t-Bu | $NO_2$ | p-Cl | 2 |
| H | $NO_2$ | p-F | 3 |
| H | $NO_2$ | p-Ph | 2 |
| H | $NO_2$ | p-OH | 2 |
| Me | $NO_2$ | p-$NO_2$ | 1 |
| Et | $NO_2$ | p-CN | 2 |
| n-Pr | $NO_2$ | p-$NMe_2$ | 3 |
| i-Pr | $NO_2$ | p-NHMe | 4 |
| n-Bu | $NO_2$ | p-$CO_2H$ | 2 |

TABLE 6-continued

| $R^6$ | $R^7$ | $R^8$ | n |
|---|---|---|---|
| i-Bu | $NO_2$ | m-$CO_2Et$ | 2 |
| t-Bu | $NO_2$ | m-OMe | 2 |
| n-Pen | $NO_2$ | p-$NO_2$ | 2 |
| n-Hex | $NO_2$ | p-$NMe_2$ | 2 |
| Me | $NO_2$ | p-NHMe | 2 |
| H | Cl | p-$NH_2$ | 2 |
| H | F | p-Et | 2 |
| H | Br | p-Pr | 2 |
| H | CN | p-$CH_2OMe$ | 2 |

The compound according to the present invention has asymmetric carbon atoms at 3-position and 4-positon, thus optical isomers thereof based on the asymmetric carbon atoms are present, which can be used in the application of the present invention similar to racemate thereof. Further, a cis or trans isomer based on configuration at 3-position and 4-position may be included, but the trans isomer is preferable.

Further, when the compounds can form their salts, the pharmaceutically acceptable salts can be also used as active ingredients.

As pharmaceutically acceptable salts, there may be mentioned hydrochlorides, hydrobromides, sulfates, methanesulfonates, acetates, benzoates, tartrates, phosphates, lactates, maleates, fumarates, malates, gluconates and salicylates, etc.

Preferably, there may be mentioned hydrochlorides and methanesulfonates.

Then, the preparation method of the compound according to the present invention is illustrated.

Of the compounds of the formula (I), those wherein $R^3$ represents a hydroxyl group, which are the compounds of formula (I-a), can be obtained by reacting a compound of the general formula (2) with a compound (3) in an inert solvent, as shown in the following reaction scheme.

The compound of the general formula (2) can be synthesized according to known methods (methods described in J. M. Evans et al., J. Med. Chem. 1984, 27, 1127, J. Med. Chem. 1986, 29, 2194, J. T. North et al., J. Org. Chem. 1995, 60, 3397, as well as Japanese Patent Application Laid-Open No. Sho 56-57785, Japanese Patent Application Laid-Open No. Sho 56-57786, Japanese Patent Application Laid-Open No. Sho 58-188880, Japanese Patent Application Laid-Open No. Hei 2-141, Japanese Patent Application Laid-Open No. Hei 10-87650 and Japanese Patent Application Laid-Open No. Hei 11-209366, etc.).

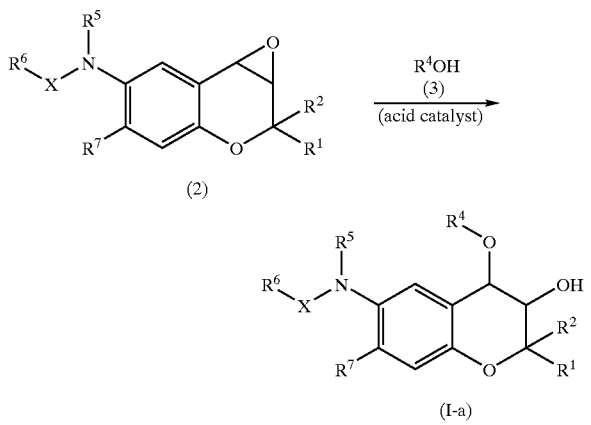

In this scheme, $R^1$, $R^2$, $R^4$, $R^5$, $R^6$, $R^7$ and X are as defined above.

As the solvents used in the reaction of the compound of the general formula (2) with the compound (3), the following may be mentioned.

There may be mentioned sulfoxide type solvents exemplified by dimethylsulfoxide; amide type solvents exemplified by dimethylformamide or dimethylacetamide; ether type solvents exemplified by ethyl ether, dimethoxyethane or tetrahydrofuran; halogen type solvents exemplified by dichloromethane, chloroform and dichloroethane; nitrile type solvents exemplified by acetonitrile and propionitrile; aromatic hydrocarbon type solvents exemplified by benzene and toluene; hydrocarbon type solvents exemplified by hexane and heptane; and ester type solvents exemplified by ethyl acetate. Further, the reaction can be carried out in the absence of a solvent. Preferably, ether type solvents and nitrile type solvents may be mentioned.

The reaction temperature is generally from −80° C. to the reflux temperature of the reaction solvent, preferably from −10° C. to 100° C.

The molar ratio of the reaction materials is within the range of 0.5–4.0, preferably 1.0–2.0, for the compound (3)/the compound (2).

An acid catalyst may be used in the reaction.

As the acid catalysts used, there may be mentioned inorganic acids exemplified by hydrochloric acid and sulfuric acid, as well as Lewis acids exemplified by aluminum chloride, titanium tetrachloride, boron trifluoride diethyl ether complex, perchloric acid, lithiumperchlorate and ytterbium trifluoromethanesulfonate, etc.

Preferably, there may be mentioned sulfuric acid and perchloric acid.

Of the compounds of the general formula (I), those other than the compounds of formula (I-a) described above (those of the formula (I) wherein $R^3$ represents a $C_{1-6}$ alkylcarbonyloxy group) can be prepared by the methods similar to those described in Japanese Patent Application Laid-Open No. Sho 52-91866 and Japanese Patent Application Laid-Open No. Hei 10-87650, etc.

Syntheses of optically active compounds included in the compounds of the general formula (I) can be attained by utilizing optical resolution methods (Japanese Patent Application Laid-Open No. Hei 3-141286, U.S. Pat. No. 5,097,037 and European Patent No. 409165). Further, syntheses of optically active compounds of the general formula (2) can be attained by utilizing asymmetrical synthetic methods (Japanese National Publication No. Hei 5-507645, Japanese Patent Application Laid-Open No. Hei 5-301878, Japanese Patent Application Laid-Open No. Hei 7-285983, European Patent Application Laid-open No.535377, and U.S. Pat. No. 5,420,314).

As described above, we, inventors, found that the compound of the general formula (I) has the strong prolongation effect on the functional refractory period. The prolongation effect on the functional refractory period is one of the functions of antiarrhythmic action and an important indicator that can be extrapolated to efficiency for clinical arrhythmia. Conventional antiarrhythmic agents having the prolongation effect on the functional refractory period as the main function (such as d-sotalol belonging to Class III of the antiarrhythmic agent classification according to Vaughan Williams) have quite dangerous arrhythmic inducing actions that can result in sudden death such as torsades de pointes based on extension of ventricular muscle action potential relating to the prolongation effect on the functional refractory period, which become the therapeutic problems for arrhythmia based on atrium (such as supraventricular tachycardia, atrial flutter and atrial fibrillation). In order to solve the problems, we, inventors, carried out searching and studying of compounds having the prolongation effect on the functional refractory period more selective for atrium muscle than for ventricular muscle, and found that the compound of the general formula (I) has the prolongation effect on the functional refractory period selective for atrium muscle without any influence on the functional refractory period of ventricular muscle and action potential parameters. The difference between the present invention by the inventors and the known techniques is to provide the prolongation effect on the functional refractory period selective for atrium muscle by the compound, which is shown by the following facts; without any influence on the action potential sustaining period of removed ventricular muscle and without any influence on the electrocardiogram QT of anesthetized animal. From the above, the compounds of the present invention have no arrhythmic inducing action in ventricular muscle, thus they can provide possibilities of more safe uses for arrhythmia based on atrium muscle than known techniques. The technique according to the present invention is useful for therapeutic or preventive uses as anti-atrial fibrillation agents, anti-atrial flutter agents and anti-atrial tachycardia agents relating to paroxysmal, chronic, preoperative, intraoperative or postoperative atrial arrhythmia, prevention of proceeding to embolus based on atrial arrhythmia, prevention of proceeding to ventricular arrhythmia or tachycardia originated from atrial arrhythmia or tachycardia, and prevention of the life prognosis worsening based on the preventive action for atrial arrhythmia or tachycardia which can be proceeded to ventricular arrhythmia or tachycardia.

The present invention provides a pharmaceutical composition or veterinary pharmaceutical composition containing the compound of the generally formula (I) in an effective amount for these treatments.

As administering forms of the compound according to the present invention, there may be mentioned parenteral administrations by means of injections (subcutaneous, intravenous, intramuscular and intraperitoneal injections), ointments, suppositories and aerosol, or oral administrations by means of tablets, capsules, granules, pills, syrups, solutions, emulsions and suspensions, etc.

The above-mentioned pharmaceutical or veterinary pharmaceutical composition contains the compound according to the present invention in an amount of about 0.01–99.5%, preferably about 0.1–30%, of the total composition weight.

In addition to the compound according to the present invention or the composition containing the compound, other pharmaceutically or veterinary pharmaceutically active compounds may be contained.

Further, these compositions may contain the plurality of compounds according to the present invention.

A clinical administration amount varies depending on age, weight and sensitivity of the patient, extent of condition of the patient, etc. and an effective administration amount is generally about 0.003–1.5 g, preferably 0.01–0.6 g, per day for adult. If necessary, however, the amount outside of the above-mentioned range may be used.

The compound according to the present invention is formulated for administration by conventional pharmaceutical means.

That is, tablets, capsules, granules and pills for oral administration are prepared by using excipients such as sucrose, lactose, glucose, starch and mannitol; binders such as hydroxypropyl cellulose, syrup, gum arabic, gelatin, sorbitol, tragacanth, methyl cellulose and polyvinyl pyrrolidone; disintegrators such as starch, carboxymethyl cellulose or its calcium salt, crystal cellulose powder and polyethylene glycol; lubricants such as talc, magnesium or calcium stearate, and silica; lubricaing agents such as sodium laurate and glycerol, etc.

Injections, solutions, emulsions, suspensions, syrups and aerosols are prepared by using solvents for the active ingredients such as water, ethyl alcohol, isopropyl alcohol, propylene glycol, 1,3-butylene glycol and polyethylene glycol; surfactants such as sorbitan fatty acid ester, polyoxyethylene sorbitan fatty acid ester, polyoxyethylene fatty acid ester, polyoxyethylene ether of hydrogenated castor oil and lecithin; suspending agents such as carboxymethyl sodium salt, cellulose derivatives such as methyl cellulose, tragacanth, and natural rubbers such as gum arabic; and preserves such as p-hydroxybenzoic acid esters, benzalkonium chloride and sorbic acid salts, etc.

For ointments that are transdermally adsorptive pharmaceutics, white vaseline, liquid paraffin, higher alcohols, Macrogol ointments, hydrophilic ointments and aqueous gel-type bases are, for example, used.

Suppositories are prepared by using, for example, cocoa fats, polyethylene glycol, lanolin, fatty acid triglyceride, coconut oil and Polysorbate etc.

BEST MODE FOR CARRYING OUT THE INVENTION

The present invention is illustrated in detail by the Examples as follows, but the present invention is not limited to these Examples.

SYNTHESIS EXAMPLES

Synthesis Example 1

Trans-6-acetylamino-3,4-dihydro-2,2-dimethyl-4-(2-phenylethoxy)-2H-1-benzopyran-3-ol

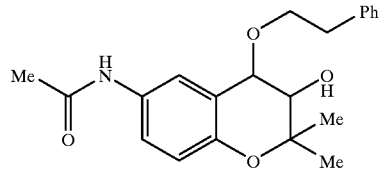

To a solution of 6-acetylamino-3,4-epoxy-3,4-dihydro-2,2-dimethyl-2H-1-benzopyran (0.50 g, 2.1 mmol) and 2-phenethyl alcohol (0.50 mL, 4.2 mol) in acetonitrile (2.5 mL), a catalytic amount of concentrated sulfuric acid was added at the room temperature and stirred at the room temperature for 5 hours. Thereto, ethyl acetate was added, and the formed organic phase was washed with water, an aqueous saturated sodium hydrogencarbonate solution and an aqueous saturated sodium chloride solution, and dried over anhydrous sodium sulfate. After the solvent was distilled off and the residue was purified by silica gel column chromatography (chloroform: ethyl acetate=1:1), the obtained pink amorphous substance was recrystallized from hexane-ethyl acetate, to obtain the intended substance as pink crystals (yield; 40%).

mp.: 141.2–143.2° C. $^1$H-NMR (CDCl$_3$) δ: 1.18 (s, 3H), 1.39 (s, 3H), 2.15 (s, 3H), 2.92–2.96 (m, 2H), 3.68 (d, J=8.2 Hz, 1H), 3.85–3.98 (m, 2H), 4.32 (d, J=8.2 Hz, 1H), 6.70 (d, J=8.8 Hz, 1H), 6.84 (d, J=1.8 Hz, 1H), 7.27–7.38 (m, 6H); MS (EI) m/z; 355 [M]$^+$, 105 (bp).

By the similar method, the following compounds were obtained. (Synthesis Examples 2–16, wherein Synthesis Example 14 is for (−) form of the compound obtained in Synthesis Example 1, Synthesis Example 15 is for (+) form of the compound obtained in Synthesis Example 1, and Synthesis Example 16 is for (+) form of the compound obtained in Synthesis Example 13.)

Synthesis Example 2

Trans-6-acetylamino-3,4-dihydro-2,2-dimethyl-7-nitro-4-(2-phenylethoxy)-2H-1-benzopyran-3-ol

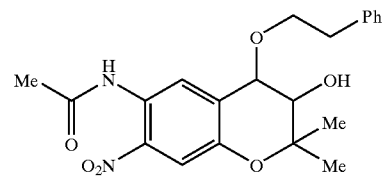

Yield: 30%; mp.: 123.5–127.0° C.; $^1$H-NMR (CDCl$_3$) δ: 1.20 (s, 3H), 1.39 (s, 3H), 1.92 (d, J=3.5 Hz, 1H), 2.27 (s, 3H), 2.98–3.02 (m, 2H), 3.63 (dd, J=3.5, 8.2 Hz, 1H), 3.91–3.97 (m, 1H), 4.15–4.20 (m, 1H), 4.33 (d, J=8.2 Hz, 1H), 7.23–7.35 (m, 5H), 7.60 (s, 1H), 8.69 (s, 1H), 9.90 (bs, 1H); MS (EI) m/z; 400 [M]$^+$, 105 (bp).

Synthesis Examples 3–16

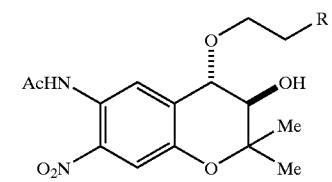

| Synthesis example No. | R |
|---|---|
| 3 | 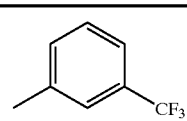 |

-continued

| Synthesis example No. | R |
|---|---|
| 4 | 4-Cl-C6H4- |
| 5 | 4-F-C6H4- |
| 6 | 3-F-C6H4- |
| 7 | 3-Cl-C6H4- |
| 8 | 4-OMe-C6H4- |
| 9 | 2,6-F,Cl-C6H3- (2-F, 6-Cl) |
| 10 | 2-Cl-C6H4- |
| 11 | 2-F-C6H4- |
| 12 | 2-CF3-C6H4- |
| 13 | 4-OH-C6H4- |
| 14 [(−) form of the compound obtained in Synthesis example 1] | C6H5- |

-continued

| Synthesis example No. | R |
|---|---|
| 15 [(+) form of the compound obtained in Synthesis example 1] | C6H5- |
| 16 [(−) form of the compound obtained in Synthesis example 13] | 4-OH-C6H4- |

Synthesis Example 3

Yield: 21%; Yellow solid; $^1$H-NMR (CDCl$_3$) δ: 1.24 (s, 3H), 1.39 (s, 3H), 2.10 (d, J=4.4 Hz, 1H), 2.26 (s, 3H), 3.06 (t, J=6.6 Hz, 2H), 3.70 (dd, A part of AB, J=7.4 and 4.4 Hz, 1H), 3.95–4.02 (m, 1H), 4.05–4.15 (m, 1H), 4.37 (d, B part of AB, J=7.4 Hz, 1H), 7.38–7.55 (m, 4H), 7.61 (s, 1H), 8.66 (s, 1H), 9.90 (s, 1H); MS (EI) m/z; 468 [M]$^+$, 354 (bp).

Synthesis Example 4

Yield: 13%; Yellow oil; $^1$H-NMR (CDCl$_3$) δ: 1.23 (s, 3H), 1.41 (s, 3H), 2.01 (d, J=4.2 Hz, 1H), 2.27 (s, 3H), 2.97 (t, J=6.5 Hz, 2H), 3.70 (dd, A part of AB, J=8.1 and 4.2 Hz, 1H), 3.90–3.98 (m, 1H), 4.00–4.15 (m, 1H), 4.36 (d, B part of AB, J=8.1 Hz, 1H), 7.21 (d, J=8.8 Hz, 2H), 7.28 (d, J=8.8 Hz, 2H), 7.60 (s, 1H), 8.63 (s, 1H), 9.89 (s, 1H); MS (FAB) m/z; 435 [M+H]$^+$.

Synthesis Example 5

Yield: 60%; Yellow amorphous substance; $^1$H-NMR (CDCl$_3$) δ: 1.22 (s, 3H), 1.41 (s, 3H), 1.98 (d, J=4.0 Hz, 1H), 2.27 (s, 3H), 2.97 (t, J=6.5 Hz, 2H), 3.69 (d, A part of AB, J=8.2 and 4.0 Hz, 1H), 3.90–4.00 (m, 1H), 4.05–4.15 (m, 1H), 4.35 (d, B part of AB, J=8.2 Hz, 1H), 6.98–7.05 (m, 2H), 7.20–7.25 (m, 2H), 7.60 (s, 1H), 8.62 (s, 1H), 9.88 (s, 1H); MS (FAB) m/z; 419 [M+H]$^+$.

Synthesis Example 6

Yield: 17%; Yellow oil; $^1$H-NMR (CDCl$_3$) δ: 1.23 (s, 3H), 1.40 (s, 3H), 2.09 (d, J=4.2 Hz, 1H), 2.27 (s, 3H), 3.00(t, J=6.6 Hz, 2H), 3.69 (d, A part of AB, J=7.6 and 4,2 Hz, 1H), 3.93–3.99 (m, 1H), 4.09–4.15 (m, 1H), 4.36 (d, B part of AB, J=7.6 Hz, 1H), 6.93–7.05 (m, 3H), 7.25–7.40 (m, 1H), 7.60 (s, 1H), 8.66 (s, 1H), 9.89 (s, 1H); MS (FAB) m/z; 419 [M+H]$^{30}$.

Synthesis Example 7

Yield: 10%; Yellow oil; $^1$H-NMR (CDCl$_3$) δ: 1.21 (s, 3H), 1.41 (s, 3H), 2.00 (s, 1H), 2.25 (s, 3H), 2.90–3.20 (m, 2H), 3.50–4.40 (m, 4(H), 7.20–7.30 (m, 4H), 7.64 (s, 1H), 8.68 (s, 1H), 9.90 (s, 1H); MS (FAB) m/z; 435 [M+H]$^+$.

Synthesis Example 8

Yield: 20%; Yellow oil; $^1$H-NMR (CDCl$_3$) δ: 1.21 (s, 3H), 1.40 (s, 3H), 1.96 (d, J=4.0 Hz, 1H), 2.27 (s, 3H), 2.94 (t, J=6.6 Hz, 2 H), 3.80 (s, 3H), 3.65 (dd, A part of AB, J=8.2 and 4.0 Hz, 1H), 3.85–3.95 (m, 1H), 4.05–4.15 (m, 1H), 4.34 (d, B part of AB, J=8.2 Hz, 1H), 6.86 (d, J=8.6 Hz and 2H), 7.19 (d, J=8.6 Hz, 2 H), 7.60 (s, 1H), 8.68 (s, 1H), 9.90 (s, 1H); MS (FAB) m/z; 431 $[M+H]^+$.

Synthesis Example 9

Yield: 25%; Yellow solid; $^1$H-NMR (CDCl$_3$) δ: 1.25 (s, 3H), 1.42 (s, 3H), 2.13 (d, J=4.3 Hz, 1H), 2.26 (s, 3H), 3.20–3.25 (m, 2H), 3.74 (dd, A part of AB, J=7.8 and 4.3 Hz, 1H), 3.85–3.95 (m, 1H), 4.00–4.10 (m, 1H), 4.41 (d, B part of AB, J=7.8 Hz, 1H), 6.95–7.00 (m, 1H), 7.10–7.20 (m, 2H), 7.61 (s, 1H), 8.69 (s, 1H), 9.89 (s, 1H); MS (FAB) m/z; 453 $[M+H]^+$.

Synthesis Example 10

Yield: 29%; Yellow amorphous substance; $^1$H-NMR (CDCl3) δ: 1.19 (s, 3H), 1.37 (s, 3H), 1.94 (d, J=3.8 Hz, 1H), 2.24 (s, 3H), 3.05–3.15 (m, 2H), 3.66 (dd, A part of AB, J=8.1 and 3.8 Hz, 1H), 3.90–4.00 (m, 1H), 4.05–4.12 (m, 1H), 4.35 (d, B part of AB, J=8.1 Hz, 1H), 7.05–7.15 (m, 2H), 7.28–7.35 (m, 2H), 7.58 (s, 1H), 8.67 (s, 1H), 9.88 (s, 1H); MS (FAB) m/z; 434 $[M]^+$.

Synthesis Example 11

Yield: 26%; Yellow amorphous substance; $^1$H-NMR (CDCl$_3$) δ: 1.22 (s, 3H), 1.41 (s, 3H), 2.00 (br s, 1H), 2.27 (s, 3H), 3.00–3.10 (m, 2H), 3.68 (br d, A part of AB, J=8.1 Hz, 1H), 3.92–4.00 (m, 1H), 4.10–4.18 (m, 1H), 4.37 (d, B part of AB, J=8.1 Hz, 1H), 7.00–7.10 (m, 2H), 7.20–7.32 (m, 2H), 7.61 (s, 1H), 8.69 (s, 1H), 9.91 (s, 1H); MS (FAB) m/z; 419 $[M+H]^+$.

Synthesis Example 12

Yield: 17%; Yellow amorphous substance; $^1$H-NMR (CDCl$_3$) δ: 1.24 (s, 3H), 1.42 (s, 3H), 2.05 (s, 1H), 2.27 (s, 3H), 3.21 (t, J=6.5 Hz, 2H), 3.73 (dd, A part of AB, J=8.0 and 4.0 Hz, 1H), 3.90–4.00 (m, 1H), 4.05–4.15 (m, 1H), 4.39 (dd, B part of AB, J=8.0 and 1.0 Hz, 1H), 7.30–7.37 (m, 1H), 7.45–7.53 (m, 2H), 7.62 (s, 1H), 7.65–7.66 (m, 1H), 8.71 (s, 1H), 9.92 (s, 1H); MS (FAB) m/z; 469 $[M+H]^+$.

Synthesis Examle 13

Yield: 30%; Yellow amorphous substance; $^1$H-NMR (CDCl$_3$) δ: 1.21 (s, 3H), 1.41 (s, 3H), 2.04 (d, J=4.0 Hz, 1H), 2.28 (s, 3H), 2.91 (t, J=6.5 Hz, 2H), 3.66 (dd, A part of AB, J=8.2 and 4.0 Hz, 1H), 3.80–3.94 (m, 1H), 4.05–4.15 (m, 1H), 4.33 (dd, B part of AB, J=8.2 and 0.7 Hz, 1H), 5.19 (br s, 1H), 6.78 (d, J=8.4 Hz, 2H), 7.12 (d, J=8.4 Hz, 2H), 7.60 (s, 1H), 8.64 (s, 1H), 9.90 (s, 1H); MS (FAB) m/z; 417 $[M+H]^+$.

Synthesis Example 14

(−) Form of the Compound Obtained in Synthesis Example 1

Said (−) form was derived from (+)-(3R*,4R*)-6-acetamide-3,4-epoxy-3,4-dihydro-2,2-dimethyl-7-nitro-2H-1-benzopyran(99% ee or more). $[\alpha]^{26}_D$=−14.9 (c 0.4, EtOH)

Synthesis Example 15

(+) Form of the Compound Obtained in Synthesis Example 1

Said (+) form was derived from (−)-(3R*,4R*)-6-acetamide-3,4-epoxy-3,4-dihydro-2,2-dimethyl-7-nitro-2H-1-benzopyran(99% ee or more) $[\alpha]^{26}_D$=+13.9 (c 0.76, EtOH)

Synthesis Example 16

(+) Form of the Compound Obtained in Synthesis Example 13

Said (+) form was derived from (+)-(3R*,4R*)-6-acetamide-3,4-epoxy-3,4-dihydro-2,2-dimethyl-7-nitro-2H-1-benzopyran(99% ee or more) $[\alpha]^{26}_D$=+5.30 (c 0.44, EtOH)

PREPARATION EXAMPLES

Preparation Example 1

| Tablet: | |
| --- | --- |
| a compound according to the invention | 10 g |
| lactose | 260 g |
| crystal cellulose powder | 600 g |
| corn starch | 350 g |
| hydroxypropyl cellulose | 100 g |
| CMC-Ca | 150 g |
| magnesium stearate | 30 g |
| total | 1,500 g |

The above-mentioned compounds were mixed by a usual method and thereafter 10,000 sugar-coated tablets each containing 1 mg of the active ingredient per a tablet were prepared.

Preparation Example 2

| Capsule: | |
| --- | --- |
| a compound according to the invention | 10 g |
| lactose | 440 g |
| crystal cellulose powder | 1,000 g |
| magnesium stearate | 50 g |
| total | 1,500 g |

The above-mentioned compounds were mixed by a usual method and thereafter filled in gelatin capsules, to prepare 10,000 capsules each containing 1 mg of the active ingredient per a capsule.

Preparation Example 3

| Soft capsule: | |
| --- | --- |
| a compound according to the invention | 10 g |
| PEG 400 | 479 g |
| saturated fatty acid triglyceride | 1,500 g |
| peppermint oil | 1 g |
| Polysorbate 80 | 10 g |
| Total | 2,000 g |

The above-mentioned compounds were mixed by a usual method and thereafter filled in No.3 soft gelatin capsules, to prepare 10,000 soft capsules each containing 1 mg of the active ingredient per a capsule.

Preparation Example 4

| Ointment: | |
|---|---|
| a compound according to the invention | 1.0 g |
| liquid paraffin | 10.0 g |
| cetanol | 20.0 g |
| white vaseline | 68.4 g |
| ethylparaben | 0.1 g |
| l-menthol | 0.5 g |
| total | 100.0 g |

The above-mentioned compounds were mixed by a usual method to obtain 1% ointment.

Preparation Example 5

| Suppository: | |
|---|---|
| a compound according to the invention | 1 g |
| Witepsol H15* | 478 g |
| Witepsol W35* | 520 g |
| Polysorbate 80 | 1 g |
| Total | 1,000 g |

(*trade name Witepsol for triglyceride type compounds)

The above-mentioned compounds were melt-mixed by a usual method, poured into suppository containers and cooled to solidify, thereby 1,000 suppositories (1 g) each containing 1 mg of the active ingredient per a suppository were prepared.

Preparation Example 6

| Injection: | |
|---|---|
| a compound according to the invention | 1 mg |
| distilled water for injection | 5 mL |

It is used by dissolving when applied.

PHARMACOLOGICAL TEST EXAMPLE

Effects of Compound on the Functional Fefractory Period in Guinea-pig Left Atrium Muscle and Right Ventricular Papillary Muscle Test Method Hearts were removed from guinea-pigs, and left atrium muscle or right ventricular papillary muscle were isolated therefrom in a Krebs-Henseleit solution aerated with 95% $O_2$+5% $CO_2$. The samples were stimulated electrically at a rate of 1 Hz and a voltage of 1.5 times of the threshold value reacted to stimulation (basic stimulation; S1) by using an electric stimulating apparatus. The contraction occurred at that time was recorded by a thermal stylus recorder via a FD pickup and a strain pressure amplifier. The functional refractory period is defined as the shortest time interval between S1 resulting from determinable contraction and an extra stimulation (S2). The time interval between S1 and S2 in the left atrium muscle sample was started from 150 msec, decreased in 10 msec steps until 100 msec, and thereafter 5 msec steps to the functional refractory period. For the right ventricular papillary muscle sample, it was started from 300 msec and decreased in 10 msec steps until the functional refractory period. Herein, S2 was set at twice of the threshold value which reacted to stimulation. The experimental temperature was 36±1° C. Herein, the solvent did not influence on any of the functional refractory periods for left atrium muscle and right ventricular papillary muscle. After determining the basic value before addition of the compound, the compound was added cumulatively, incubated for 15 minutes for respective concentration, and thereafter the functional refractory period was determined.

Results

Compounds according to the present invention exhibited strong prolongation effect on the functional refractory period (FRP) on atrium muscle.

TABLE 7

| Synthesis example No. | Prolongation effect on FRP $EC_{20}(\mu M)$ |
|---|---|
| 2 | 2.1 |

Compounds according to the present invention exhibit strong prolongation effect on the functional refractory period, thus they are useful for improvement of arrhythmia. Therefore, the present invention can provide useful drugs for treating arrhythmia.

What is claimed is:

1. A 4-oxybenzopyran derivative of the formula (I)

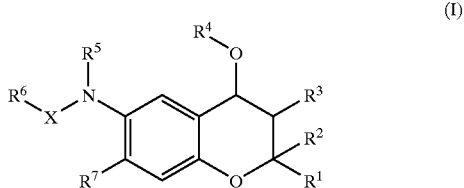

wherein, $R^1$ and $R^2$ represent each independently a hydrogen atom; a $C_{1-6}$ alkyl group in which said alkyl group may be optionally substituted with a halogen atom, a $C_{1-6}$ alkoxy group or a hydroxyl group; or a phenyl group in which said phenyl group may be optionally substituted with a halogen atom, a hydroxyl group, a nitro group, a cyano group, a $C_{1-6}$ alkyl group or a $C_{1-6}$ alkoxy group;

$R^3$ represents a hydroxyl group or a $C_{1-6}$ alkylcarbonyloxy group;

$R^4$ represents a hydrogen atom, a $C_{3-6}$ cycloalkyl group, a $C_{1-6}$ alkyl group, a $C_{1-6}$ alkylcarbonyl group, a $C_{1-6}$ alkylaminocarbonyl group or a di-$C_{1-6}$ alkylaminocarbonyl group in which said $C_{1-6}$ alkyl group, said $C_{1-6}$ alkylcarbonyl group, said $C_{1-6}$ alkylaminocarbonyl group and said di-$C_{1-6}$ alkylaminocarbonyl group may be each optionally substituted with a halogen atom, a $C_{1-6}$ alkoxy group, a $C_{1-6}$ alkoxy group substituted by a halogen atom; a carboxyl group, a $C_{1-6}$ alkoxycarbonyl group, a hydroxyl group, or an aryl group selected from the group consisting of: phenyl, biphenyl, naphthyl, anthryl and phenanthryl, in which said aryl group may be optionally substituted with $(R^8)_m$, in which $R^8$ represents a halogen atom, a hydroxyl group, a $C_{1-6}$ alkyl group, a $C_{1-6}$ alkyl group substituted by a halogen atom or a $C_{1-6}$ alkoxy group; a $C_{1-6}$ alkoxy group, a $C_{1-6}$ alkoxy group substituted by a halogen atom; or $R^8$ represents a nitro group, a cyano group, a formyl group, a formamide group, an amino group, a $C_{1-6}$ alkylamino group, a di-$C_{1-6}$ alkylamino group, a $C_{1-6}$ alkylcarbonylamino group, a $C_{1-6}$ alkylsulfonylamino group, an aminocarbonyl group, a $C_{1-6}$ alkylaminocarbonyl group, a di-$C_{1-6}$ alkylaminocarbonyl group, a $C_{1-6}$ alkylcarbonyl group, a $C_{1-6}$ alkoxycarbonyl group, an aminosulfonyl group, a $C_{1-6}$ alkylsulfonyl group, a carboxyl group or an arylcarbonyl group, m represents an integer of 1–3 and each $R^8$ may be the same or different if m represents 2 or 3;

$R^5$ represents a hydrogen atom or a $C_{1-6}$ alkyl group;

X is absent or represents C=O or $SO_2$;

$R^6$ represent a hydrogen atom, a $C_{1-6}$ alkyl group in which said alkyl group may be optionally substituted with a halogen atom, a hydroxyl group or a $C_{1-6}$ alkoxy group; or a $C_{3-6}$ cycloalkyl group;

$R^7$ represents a hydrogen atom, a halogen atom, a nitro group or a cyano group;

or a pharmaceutically acceptable salt thereof.

2. A 4-oxybenzopyran derivative or pharmaceutically acceptable salt thereof according to claim 1, wherein $R^1$ and $R^2$ represent both methyl groups and $R^3$ represents a hydroxyl group.

3. A 4-oxybenzopyran derivative or pharmaceutically acceptable salt thereof according to claim 2, wherein X represents C=O and $R^5$ represents a hydrogen atom.

4. A 4-oxybenzopyran derivative or pharmaceutically acceptable salt thereof according to claim 3, wherein $R^4$ represents an alkyl group and $R^7$ represents a nitro group.

5. A drug characterized by comprising a 4-oxybenzopyran derivative or pharmaceutically acceptable salt thereof according to claim 1 as an active ingredient.

6. A drug for treating arrhythmia characterized by comprising a 4-oxybenzopyran derivative or pharmaceutically acceptable salt thereof according to claim 1 as an active ingredient.

* * * * *